(12) United States Patent
Nakamura

(10) Patent No.: US 10,649,200 B2
(45) Date of Patent: May 12, 2020

(54) PRODUCTION METHOD FOR BINOCULAR LOUPE

(71) Applicant: Shoichi Nakamura, Nagano-ken (JP)

(72) Inventor: Shoichi Nakamura, Nagano-ken (JP)

(73) Assignees: Shoichi Nakamura, Higashichikuma-Gun, Nagano-Ken (JP); ACP JAPAN CO., LTD., Tokyo (JP)

( * ) Notice: Subject to any disclaimer, the term of this patent is extended or adjusted under 35 U.S.C. 154(b) by 353 days.

(21) Appl. No.: 15/598,989

(22) Filed: May 18, 2017

(65) Prior Publication Data

US 2018/0335617 A1    Nov. 22, 2018

(51) Int. Cl.

| G02B 23/12 | (2006.01) |
|---|---|
| G02B 25/00 | (2006.01) |
| G02C 7/08 | (2006.01) |
| A61B 90/00 | (2016.01) |
| A61B 90/50 | (2016.01) |
| G02B 7/00 | (2006.01) |

(52) U.S. Cl.
CPC ......... G02B 23/125 (2013.01); G02B 25/004 (2013.01); G02C 7/088 (2013.01); *A61B 2090/3616* (2016.02); *A61B 2090/502* (2016.02); *G02B 7/003* (2013.01)

(58) Field of Classification Search
CPC .... G02B 23/125; G02B 25/004; G02B 7/003; G02C 7/088; A61B 2090/3616; A61B 2090/502

USPC .......................................................... 359/419
See application file for complete search history.

(56) References Cited

U.S. PATENT DOCUMENTS

2013/0188128 A1 * 7/2013 Divo .................... G02C 13/005
                                                                  351/204

FOREIGN PATENT DOCUMENTS

JP          5311601 B1      10/2013
JP       2014044391 A  *    3/2014

* cited by examiner

*Primary Examiner* — Thomas K Pham
*Assistant Examiner* — Mitchell T Oestreich
(74) *Attorney, Agent, or Firm* — Manabu Kanesaka

(57) ABSTRACT

In a binocular loupe production method capable of attaching a loupe to a carrier lens at a correct downward attachment angle by measuring a forward tilting angle of a worker accurately, a square marker is attached to a frame having the carrier lens, and the face of a user wearing the frame and looking at a working operation point P located below while assuming a working posture taken when he or she uses the binocular loupe is photographed from the working operation point P. A forward tilting angle α of the carrier lens is calculated on the basis of the degree of change from the square shape to a trapezoidal shape of the marker in an oblique image of the face photographed from below, and a downward attachment angle r at which a loupe is attached to the carrier lens is determined according to the forward tilting angle α.

33 Claims, 17 Drawing Sheets

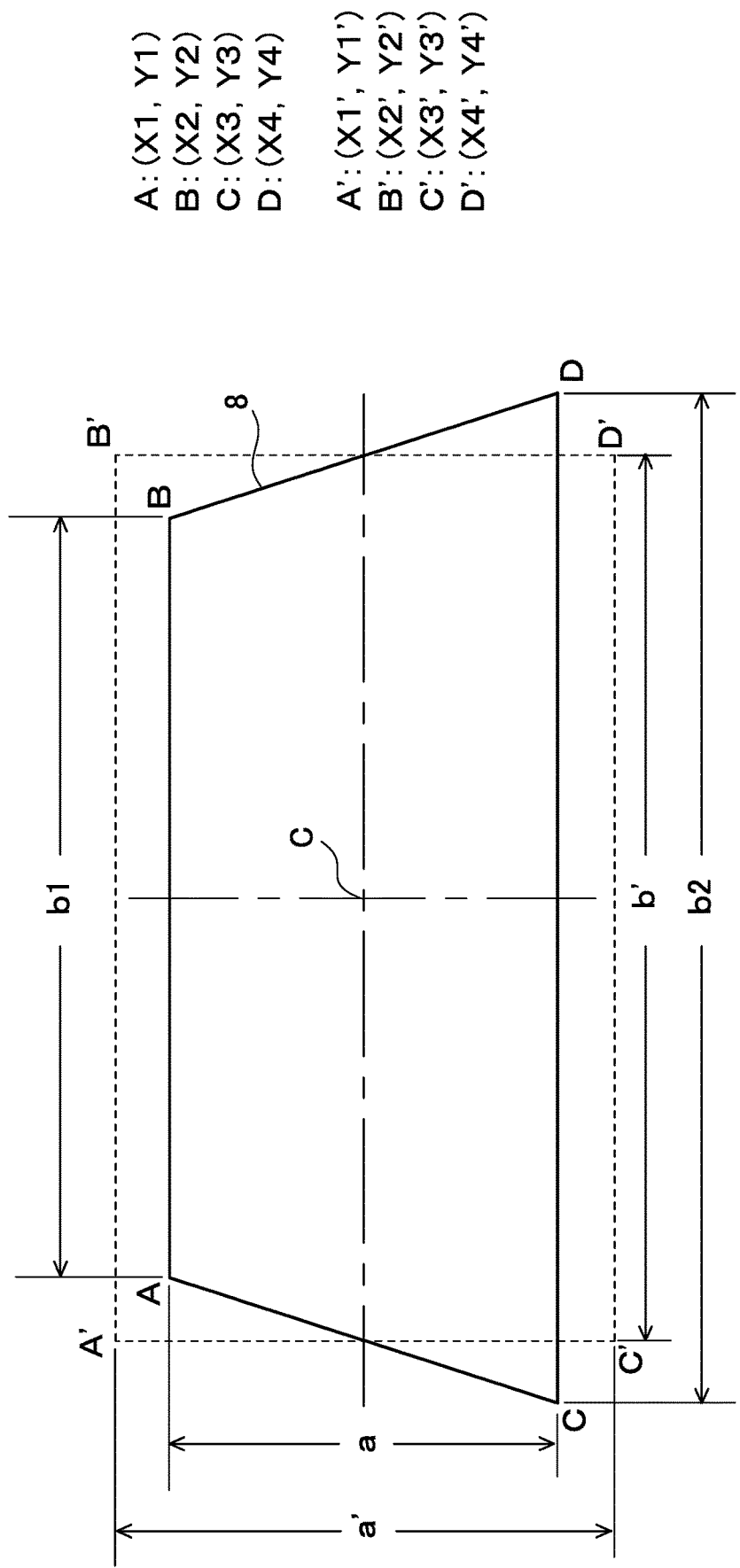

PRODUCTION METHOD FOR BINOCULAR LOUPE

BACKGROUND OF THE INVENTION

Field of the Invention

The present invention relates to a binocular loupe used for medical surgery or precision machining and, more particularly to a production method for a binocular loupe in which a loupe is attached to a carrier lens fitted in a frame.

Description of the Related Art

Binocular loupes have been widely used as a means for magnifying a local visual object at hand for enhancing visibility in various fields such as medical services, precision machining, and Jewelry processing. In these fields, a visual object needs to be viewed with high accuracy.

As illustrated in FIG. 1, a lens fitting type binocular loupe 10 for general use includes a frame 1 having the same structure as that of glasses for adjusting user's eyesight, a loupe 2 as a binocular loupe main body for magnifying the image of a work object, a carrier lens 5 fitted in the frame 1 and used for attachment of the loupe 2, an attachment part 3 for attaching the loupe 2 to the carrier lens 5, and a frame temple part 6 for allowing the binocular loupe 10 to be worn on the user's face. The loupe 2 is inserted into an opening formed in the surface of the carrier lens 5 and fixed thereto by the attachment part 3.

FIG. 2 is an explanatory view illustrating a state where a worker wears the binocular loupe 10. Like ordinary glasses, the binocular loupe 10 can be worn on the worker's face with the frame temple part 6 of the frame 1 put on his or her ear.

As illustrated in FIG. 3, during a procedure, a worker looks at a leading end (working operation point P) of an instrument being held by his or her hand in a forward tilting posture and observes the working operation point P while magnifying the image thereof through the loupe 2. Thus, the loupe 2 is attached to the carrier lens 5 at a vertically downward (to the lower edge side of the frame) inclination angle (downward attachment angle r) relative to the plane of the carrier lens 5 as illustrated in FIG. 2 and a horizontally inward (to the nose pad side) inclination angle (left and right inward attachment angles p and q) relative thereto as illustrated in FIG. 4.

However, when the thus configured binocular loupe 10 is used in the medical fields concerned with human life, highly accurate visibility needs to be ensured. To this end, it is necessary to measure a correct pupil position, the downward attachment angle r and the inward attachment angles p and q according to each user and to attach the loupe 2 to the carrier lens 5 on the basis of the measurement results.

To respond such requirements, the following binocular loupe production method is known. In this method: 1) an actual working posture (posture during surgery) is assumed by a worker (surgeon) wearing the frame 1; 2) the distance from the working operation point P to the frame 1 and that from the working operation point P to the left and right pupils are actually measured by a measuring means, or calculated from a photographed image; and 3) the loupe 2 is attached to the carrier lens 5 according to the pupil position, downward attachment angle r, and inward attachment angles p and q derived from the measurement results (see Patent Document 1).

PRIOR ART DOCUMENT

Patent Document

[Patent Document 1] Japanese Patent No. 5311601

As illustrated in FIG. 5, the downward attachment angle r can be derived from an angle β formed by sides obtained by measuring a distance M between the working operation point P and the carrier lens 5 and a horizontal direction distance N orthogonal to the vertical line passing through the carrier lens 5, respectively, and a forward tilting angle α of the carrier lens 5 when the surgeon performs surgery.

It is difficult to obtain the forward tilting angle α by actual measurement. So, in the Japanese Patent No. 5311601, the forward tilting angle α is obtained by measuring the forward tilting angle of the head part or carrier lens 5 relative to the vertical line passing through the backbone based on an image viewed from the side of a loupe wearer assuming a forward tilting posture.

However, the carrier lens 5 is not fitted to the frame temple part 6 at right angle because of the structure of the frame 1. Further, even when the wearer faces in the horizontal direction with the frame 1 put on his or her ears, the frame temple part 6 is not strictly in the horizontal state. Therefore, when the inclination angle to the vertical line is simply measured to obtain the forward tilting angle α, errors may occur.

SUMMARY OF THE INVENTION

The present invention has been made in view of the above points, and the object thereof is to provide a binocular loupe production method capable of attaching the loupe to the carrier lens at a correct downward attachment angle by measuring the forward tilting angle α of a worker with high accuracy.

A binocular loupe production method according to the present invention is a method that produces a binocular loupe by attaching a loupe to a carrier lens fitted to a frame under conditions according to a wearer of the binocular loupe, the method including: (a) a step of attaching a square marker to the frame; (b) a step of photographing, from a working operation point P located below, the face of the frame wearer who looks at the working operation point P while assuming a working posture taken when he or she is using the binocular loupe; (c) a step of detecting the marker from an oblique image of the face photographed from below; and (d) a step of calculating a forward tilting angle α of the carrier lens according to the degree of change from the square shape to a trapezoidal shape of the marker detected in the step (c) and determining, based on the forward tilting angle α, a downward attachment angle r based on which the loupe is attached to the carrier lens.

In the step (c), objects to be identified included in the photographed image are identified in the descending order of matching degree, and then the marker is detected.

In the step (d), the forward tilting angle α is determined by identifying the coordinate positions of the four corners of the marker. Specifically, the image is converted into polylines, and an object in which the angle of each of the four corners is near 90° is searched for from among objects having four corners, whereby the coordinate positions of the four corners of the marker are identified.

By identifying the above coordinate positions, it is possible to determine the forward tilting angle α on the basis of the dimensions of the upper and lower bases of the trapezoidal shape derived from the coordinate positions, the ratio of the actual vertical and horizontal dimensions of the marker, and the distance from the working operation point to the center point of the marker.

In the step (d), by determining the forward tilting angle α, it is possible to determine the downward attachment angle according to the complementary angle of the angle formed by a line extending from the working operation point to the carrier lens which is previously measured as a distance M and a horizontal line orthogonal to the vertical line passing through the carrier lens which is previously measured as a distance N and the forward tilting angle α.

The binocular loupe production method according to the present invention further includes (e) a step of identifying, from the photographed image, the X- and Y-axes coordinate positions of the respective right pupil (XR, YR) and left pupil (XL, YL) of the frame wearer who looks at the working operation point located below.

In the step (e), the positions of the pupils are detected by identifying a position where brightness changes discontinuously from the photographed image. To this end, face detection is performed by extracting image features peculiar to a face from the photographed image, followed by detection of the pupil positions from the detected face.

In this case, image features peculiar to an eye is extracted from the detected face. Then, the contour of an iris is detected by binarizing the detection image of the eye, and morphology processing is performed to detect a rectangle having the maximum brightness to detect the pupil positions.

The attachment position of the loupe to the carrier lens is determined by detecting the pupil position. At this time, the Y-coordinate value of the loupe attached to the carrier lens is preferably below the Y-coordinate values of the respective left and right pupils.

In this case, the Y-coordinate value of the loupe attached to the carrier lens is determined on the basis of an angle at which the frame wearer turns his or her cornea upward to direct the line of sight in the horizontal direction. At this time, the angle at which the cornea is turned upward is determined on the basis of the forward tilting angle α and a tilt angle θ of the carrier lens relative to the vertical line, a distance V between the cornea and carrier lens, and a distance M from the working operation point to the surface of the carrier lens.

According to the binocular loupe production method of the present invention, by photographing the marker from the working operation point located below, the square shaped marker is captured as a trapezoidal shape. Then, the tilt of the marker, i.e., the tilt of the carrier lens is detected according to the degree of change from the square shape to the trapezoidal shape, so that it is possible to correctly grasp the forward tilting angle of the wearer. Thus, the loupe can be attached to the carrier lens at an adequate downward attachment angle according to the forward tilting angle of the wearer during his or her work.

BRIEF DESCRIPTION OF THE DRAWINGS

FIG. 10 schematically illustrates a front view image of a marker attached to a frame as viewed from a working operation point;

DESCRIPTION OF THE PREFERRED EMBODIMENTS

Hereinafter, an embodiment of a binocular loupe production method will be described in detail with reference to the accompanying drawings.

In the production method according to the present invention, one who orders a binocular loupe of the present invention has a user wear the frame 1 to which the loupe 2 is not fitted and assume a working posture, and the orderer photographs the wearer's face by a camera 11 installed at the working operation point P. Then, a computer is used to process the photographing data to thereby measure the pupil position, downward attachment angle r and inward attachment angles p and q corresponding to the wearer, and the loupe 2 is attached to the carrier lens 5 according to the measurement results, whereby a binocular loupe is produced.

Figure 6:
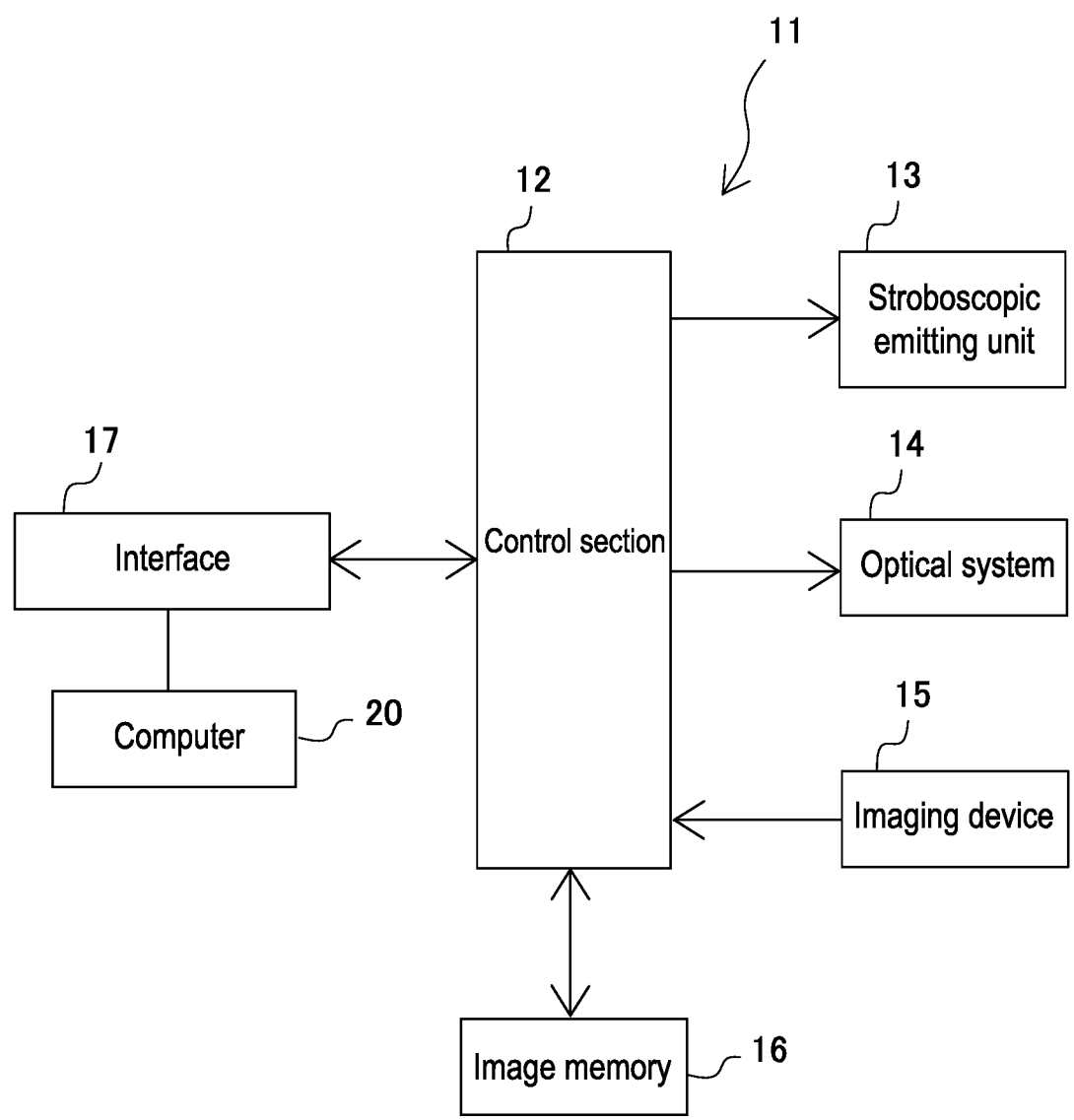
FIG. 6 is a block diagram schematically illustrating the configuration of a camera.

FIG. 6 schematically illustrates the configuration of the camera 11. The camera 11 is a digital camera including a control section 12, a stroboscopic emitting unit 13, an optical system 14, an imaging device 15, an image memory 16, a computer 20 that performs image processing, and an interface 17 for exchanging data and signals.

The control section 12 includes a program storage section that controls individual sections of the camera 11 and a CPU that executes a program stored in the program storage section. The control section 12 performs imaging magnification or focusing of the optical system 14 according to an instruction from the computer 20, storage/readout of images in/from the image memory 16, and the like.

Figure 7:
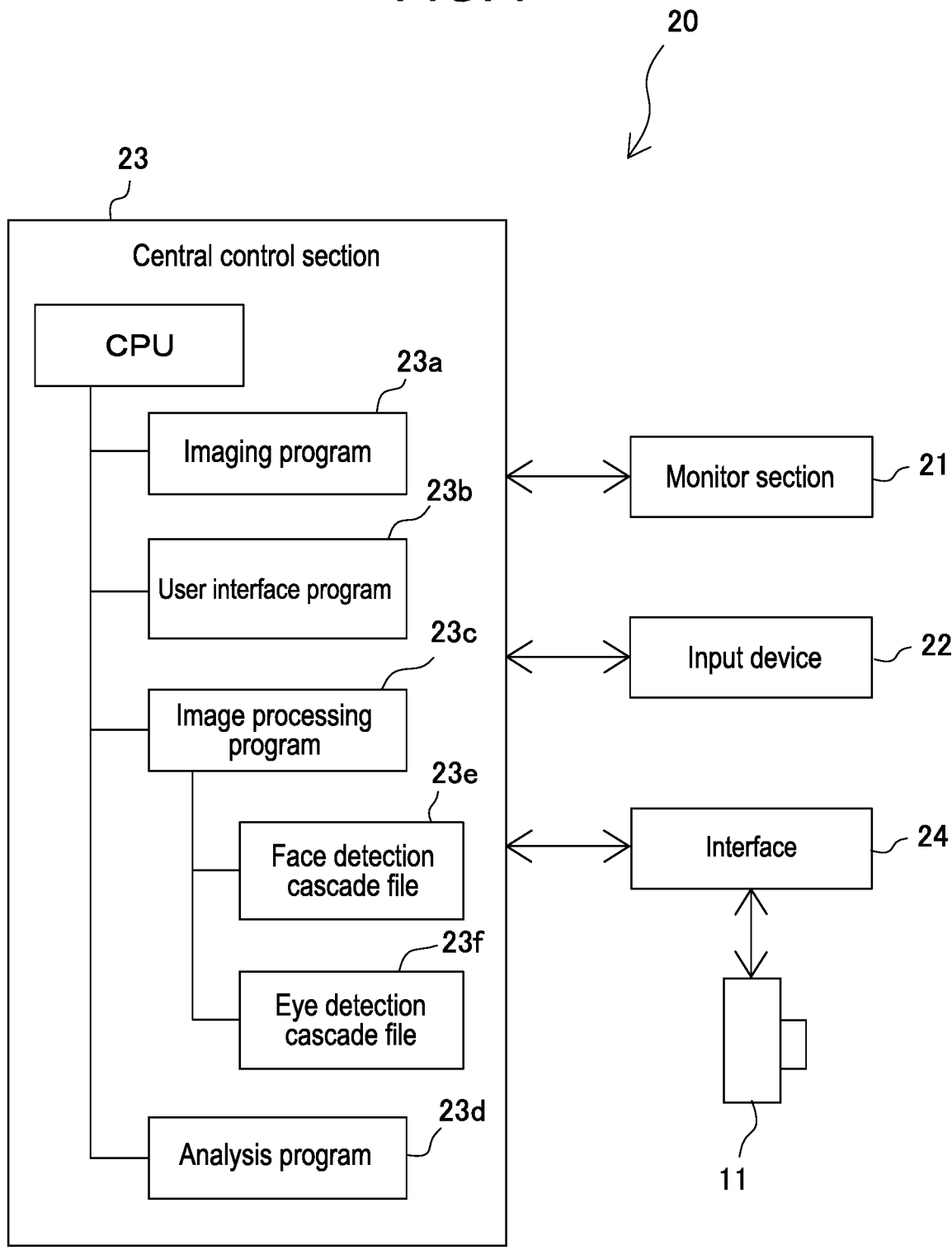
FIG. 7 is a block diagram schematically illustrating the configuration of a computer.

FIG. 7 schematically illustrates the configuration of the computer 20. The computer 20 includes a monitor section 21, an input device 22, a central control section 23 that performs predetermined arithmetic processing or control processing based on a program, and an interface 24 for exchanging data and signals with the camera 11.

The central control section 23 includes an imaging program 23*a*, a user interface program 23*b*, an image processing program 23*c*, and an analysis program 23*d*, and a central processing unit (CPU) that executes these programs. The image processing program 23*c* is a cascade classifier that classifies an object to be identified by subdividing the same in the descending order of matching degree. In the present example, the image processing program 23*c* identifies a face or eyes from an image of a person. Thus, the image processing program 23*c* includes a face detection cascade file 23*e* and an eye detection cascade file 23*f* that store therein features of faces and eyes, respectively, through learning.

When photographing a user wearing the frame 1 by the camera 11, a square marker 8 is screw-attached to a bridge 7 between both left and right lenses of the frame 1. In this case, the marker 8 is attached to the frame 1 such that the center thereof coincides with the center position of the frame 1 in the horizontal direction. The marker 8 is a white acrylic board, and engraved and painted in black excluding the peripheral edge and screwed center thereof.

The photographing is performed using the camera 11 activated by the computer 20. The central control section 23 executes the imaging program 23*a* to control operation of the camera 11 to adjust a focal length to a center point C (see FIG. 8) of the marker 8 attached to the frame 1. According to an instruction from the computer 20, the camera 11 outputs an image signal which is an electrical signal obtained by the imaging device 15 through conversion of an image captured by the optical system 14. Then, the computer 20 displays the obtained image on the monitor section 21, whereby a producer of the binocular loupe can instruct adjustment of a capturing range of the image by the camera 11, image positioning, and the like using the input device 22. The computer 20 then adjusts the image photographed by the camera 11 according to the adjustment instruction.

In response to an imaging instruction which is send from the computer 20 under the instructions of the producer, the camera 11 performs photographing by emission of strobe light from the stroboscopic emitting unit 13. Then, the imaging device 15 of the camera 11 converts a photographing light from the optical system 14 into an electrical signal and outputs it, and the control section 12 stores image data corresponding to the electrical signal in the image memory 16.

Figure 8:
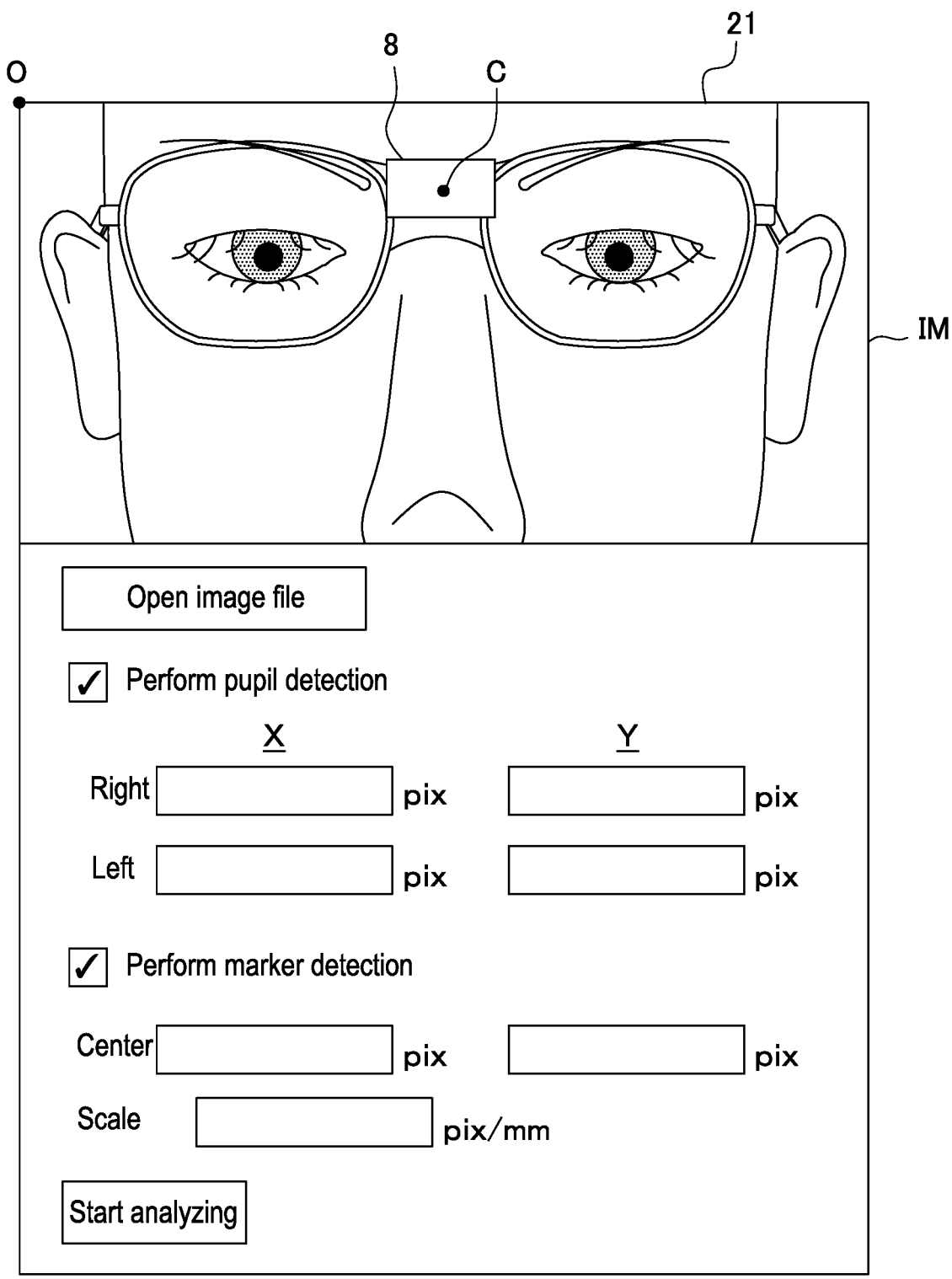
FIG. 8 schematically illustrates a user interface screen that the computer displays when processing a photographed image.

In the computer 20, when image processing operation is designated, the central control section 23 processes the user interface program 23*b* to display a user interface window illustrated in FIG. 8 on the monitor section 21. Then, when an "OPEN IMAGE FILE" button provided in the input section on this window is operated to designate an image data file of a specified wearer, the central control section 23 reads out the designated image data from the image memory 16 and displays it in an image display area IM.

Subsequently, a "PERFORM PUPIL DETECTION" button and/or a "PERFORM MARKER DETECTION" button on the user interface window are checked, and then an "ANALYSIS START" is operated. Then, the computer 20 starts analyzing the pupil position and the center position of the marker 8.

Figure 9B:
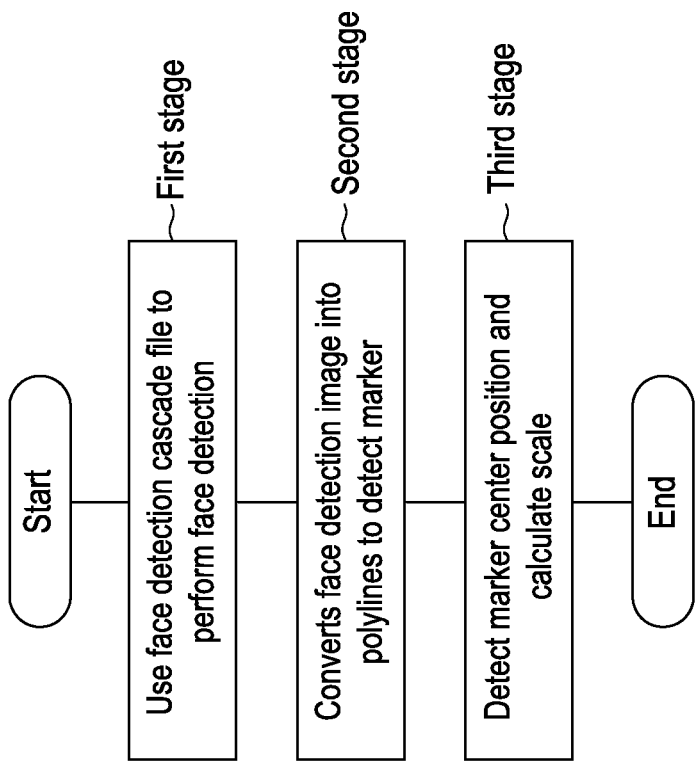
FIGS. 9A and 9B are explanatory views illustrating the processing procedures taken by a cascade type classification program.
Figure 9A:
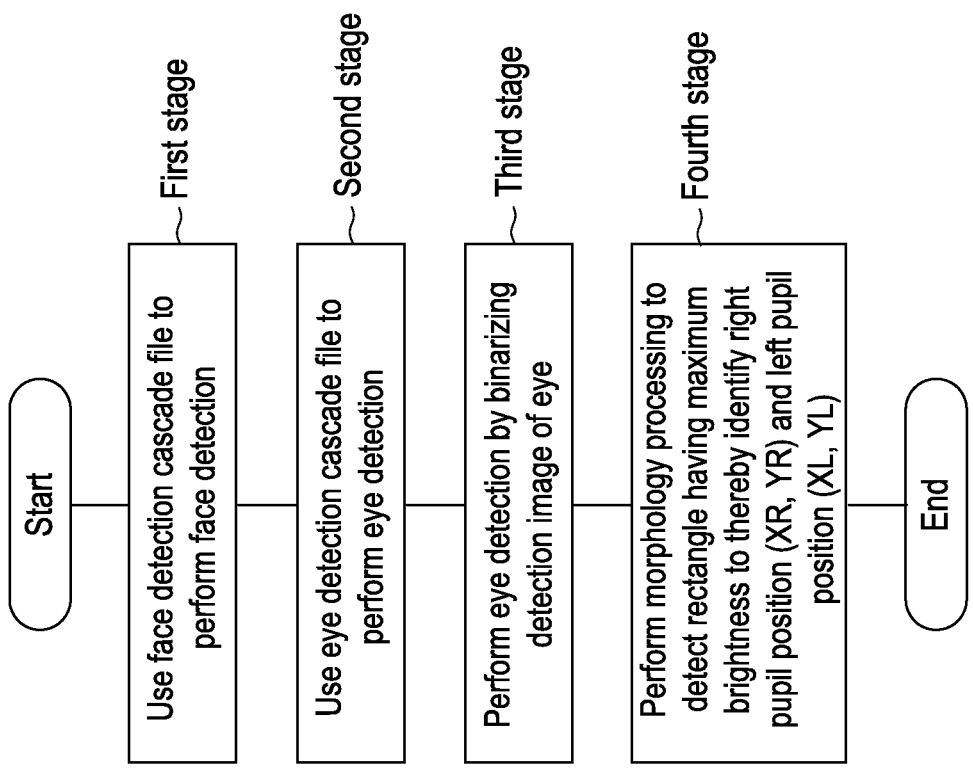

FIG. 9A illustrates the processing procedure of pupil position detection by the image processing program 23*c*. The central control section 23 processes the image processing program 23*c* to identify a position where brightness changes sharply, or discontinuously to thereby detect the pupil position. The central control section 23 uses the face detection cascade file 23*e* to perform face detection in a first stage. Specifically, in this face detection, the central control section 23 determines whether a target to be identified corresponds to a face from image features peculiar to a face. In a second stage, the central control section 23 uses the eye detection cascade file 23*f* to perform eye detection by subdividing the target to be identified. Specifically, in this eye detection, the central control section 23 determines whether a target to be identified corresponds to an eye based on image features peculiar to an eye. In a third stage, the central control section 23 detects the contour of an iris by binarizing a detection image of an eye. In a fourth stage, the central control section 23 performs morphology processing to detect a rectangle having the maximum brightness and, thereby, the computer 20 detects the coordinate position (XR, YR) of the right pupil of the wearer and coordinate position (XL, YL) of the left pupil and displays them on the window. In this case, for example, a point at the upper left corner of the image display area IM is set as a coordinate reference point O.

FIG. 9B illustrates the processing procedure of marker detection by the image processing program 23*c*. The central control section 23 uses the face detection cascade file 23*e* to perform face detection in a first stage to thereby narrow down the area where the marker 8 may exist. In a second stage, the central control section 23 converts the face detection image into polylines and extracts, from objects each having four corners, an object in which the angle of each of the four corners is near 90°, thereby recognizing the marker 8. Then, in a third stage, the computer 20 displays the coordinate position of the center of the marker 8 and a scale on the window. The scale indicates correspondence between 1 mm and the number of pixels in the image, and the central control section 23 calculates the scale on the basis of the previously input actual size of the marker 8.

After detecting the pupil position and the center position of the marker 8 in the manner as described above, the computer 20 processes the analysis program 23*d* to derive, from the detection data, a punching position, the downward attachment angle, and the inward attachment angles based on which the loupe 2 is attached to the surface of the carrier lens 5 through arithmetic operation.

[Determination of Downward Attachment Angle of Loupe]

Figure 1:
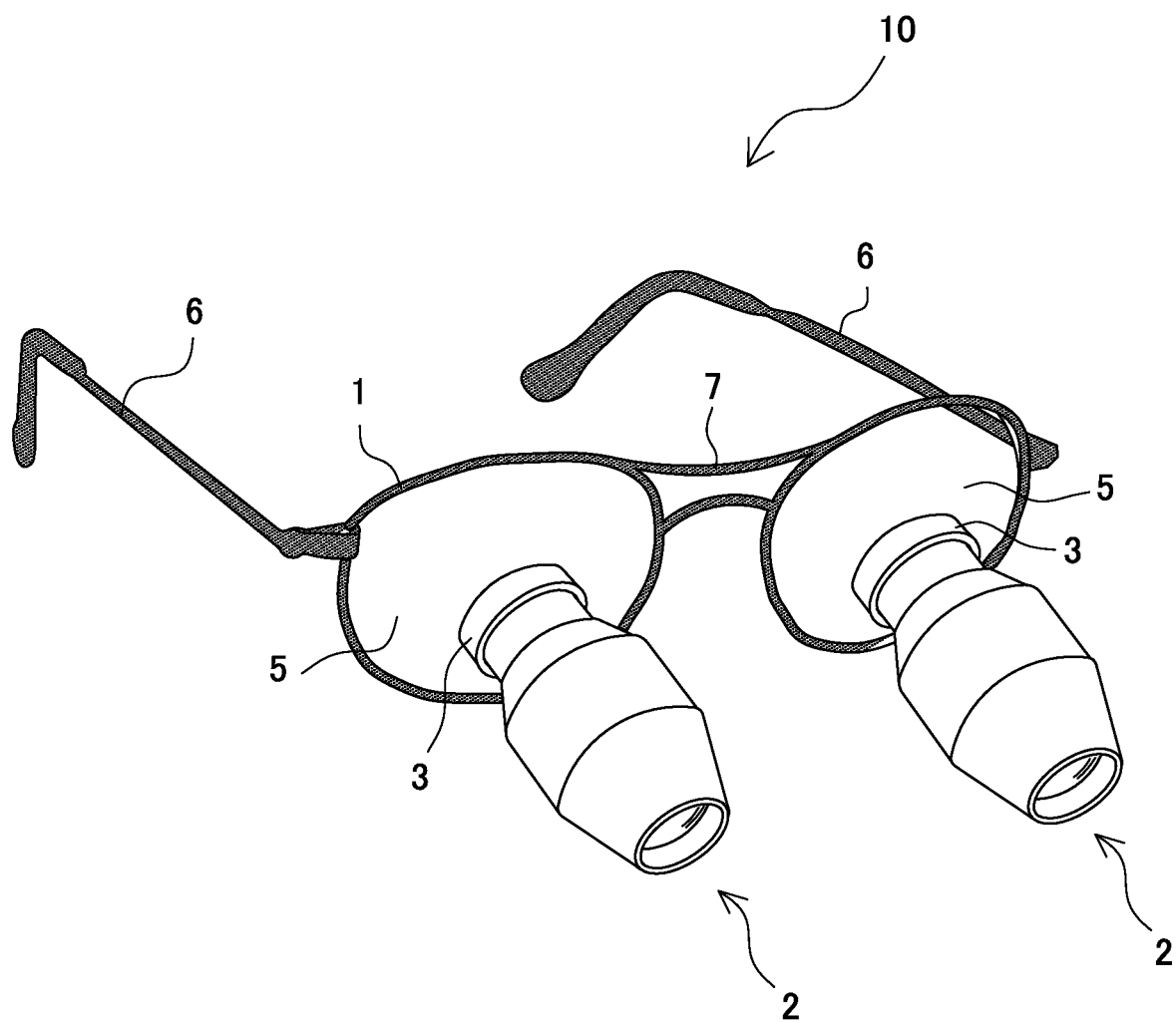
FIG. 1 is an entire configuration view of a binocular loupe.
Figure 2:
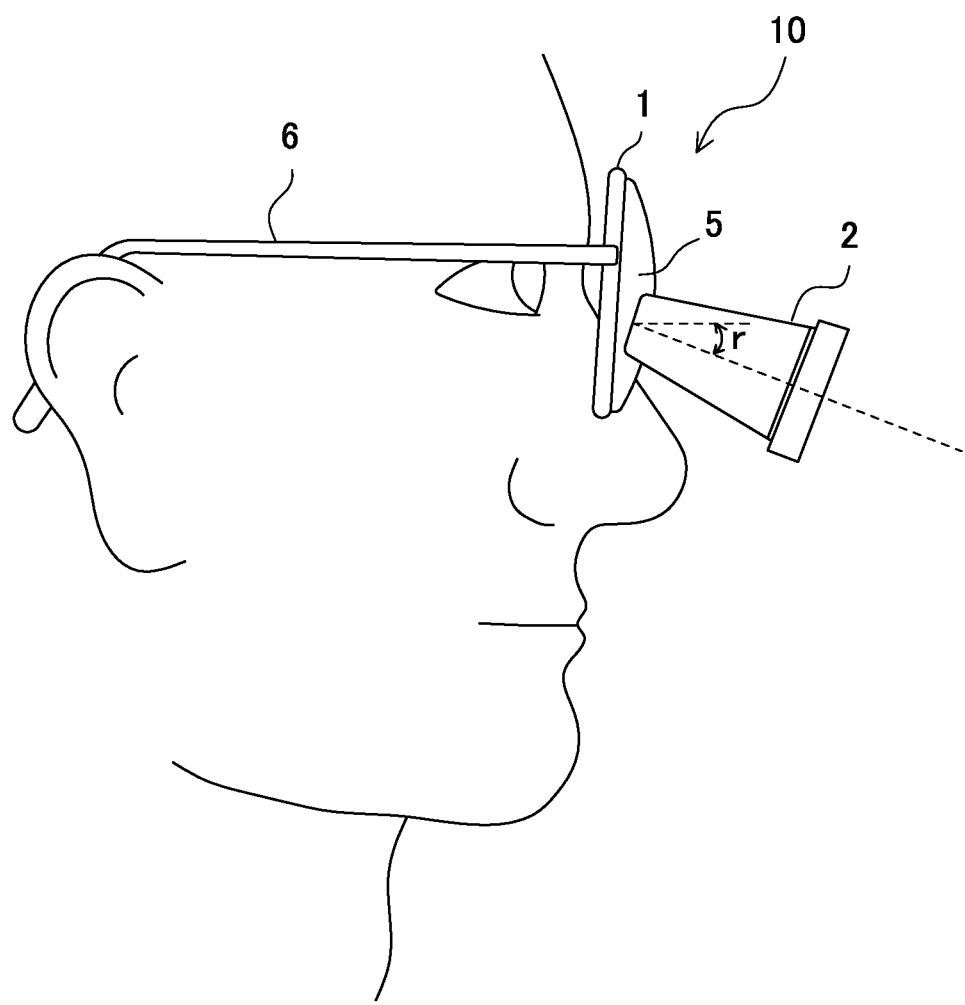
FIG. 2 is a side view illustrating a wearing state of the binocular loupe.
Figure 3:
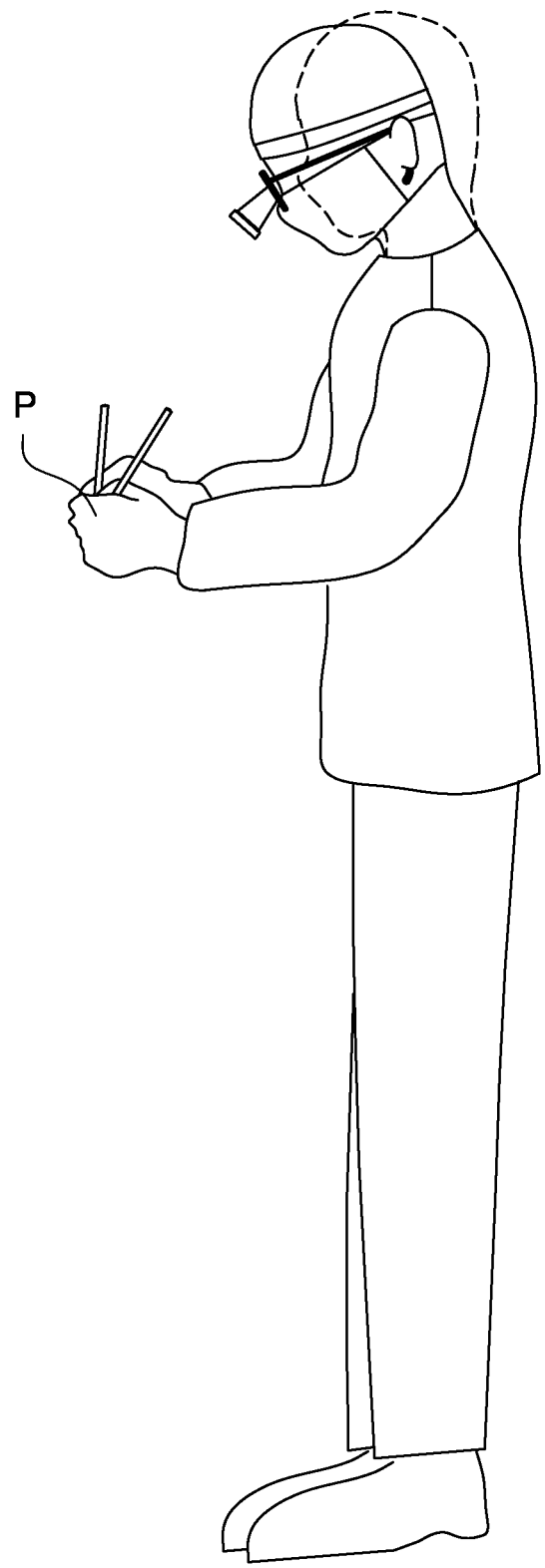
FIG. 3 is an explanatory view schematically illustrating a state where a worker wears the binocular loupe and assumes a working posture.
Figure 4:
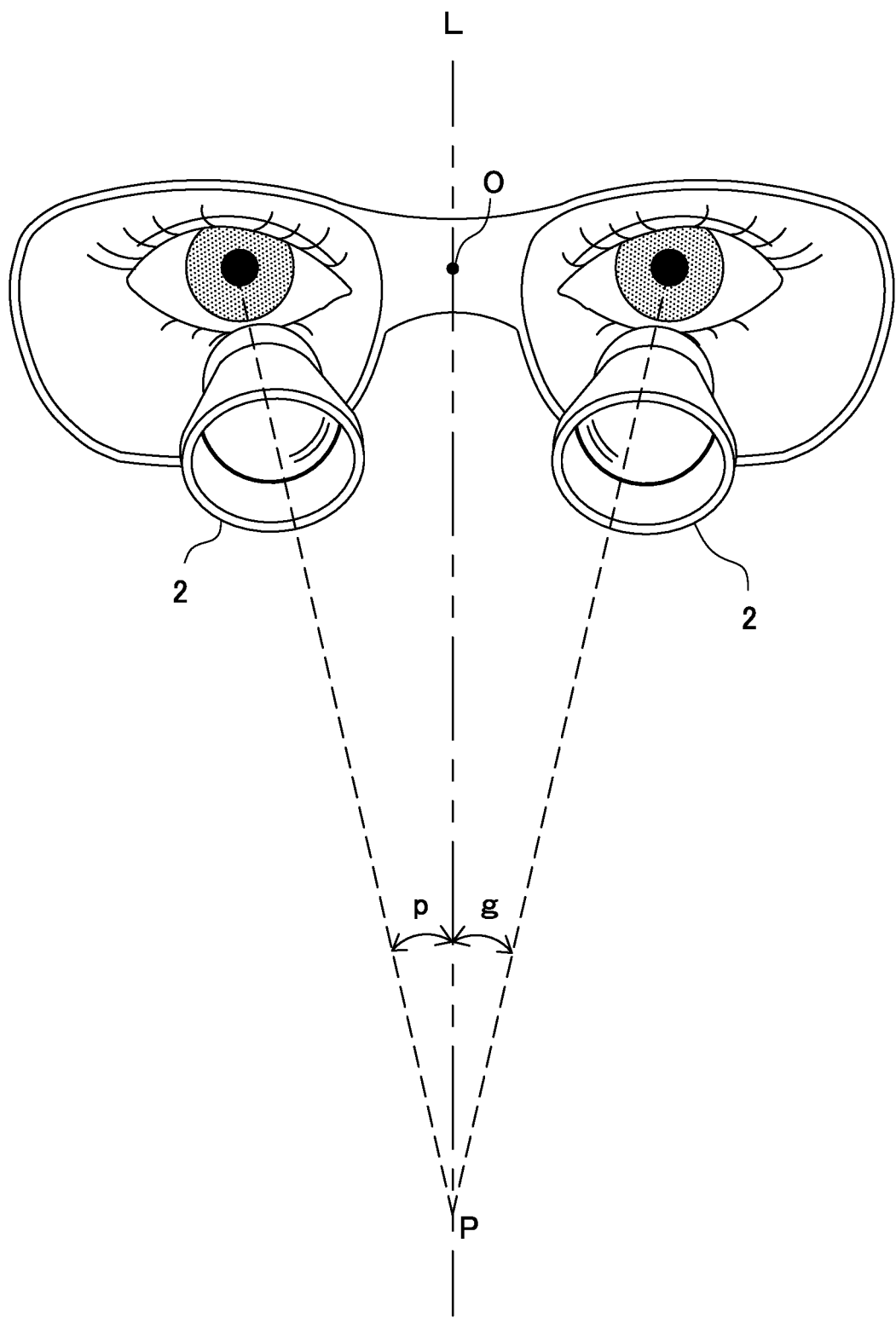
FIG. 4 is an explanatory view illustrating inward attachment angles when a loupe is attached to a carrier lens.
Figure 5:
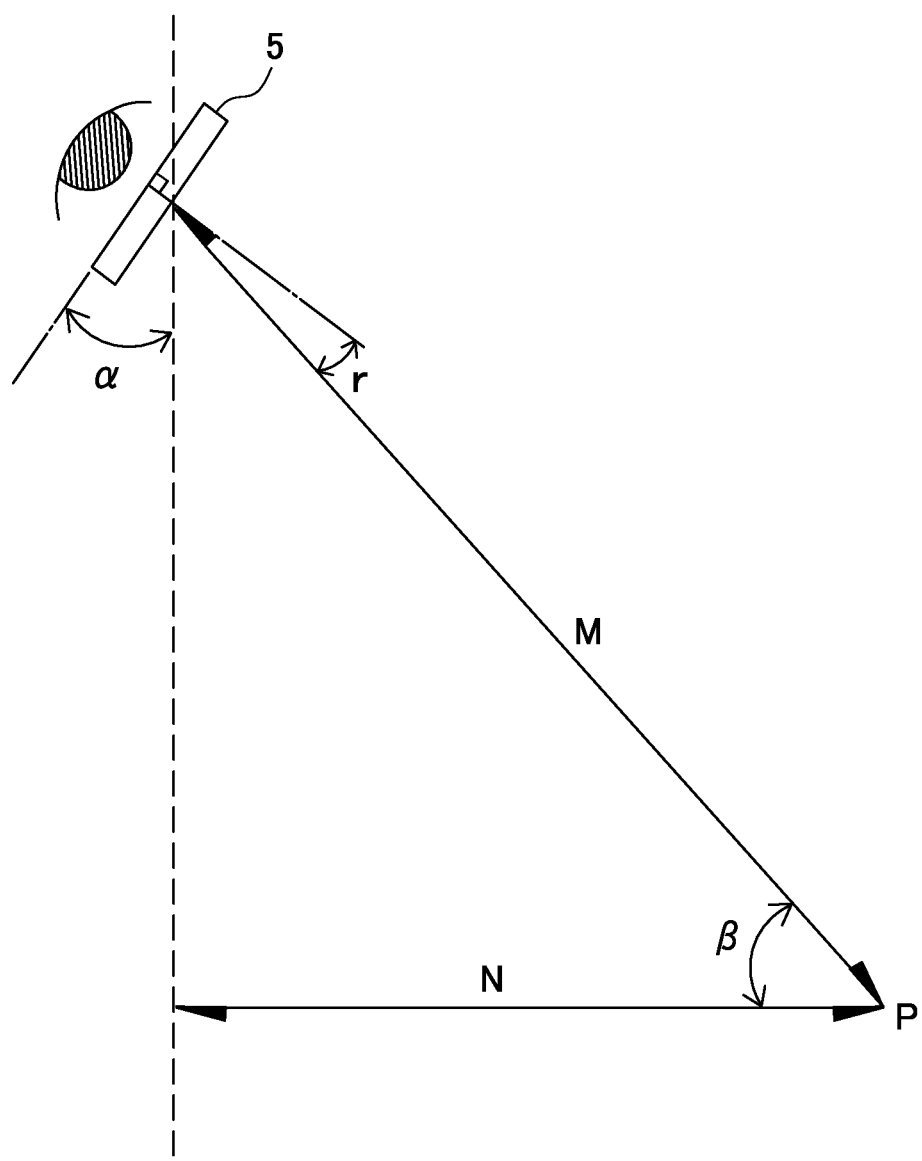
FIG. 5 is an explanatory view illustrating downward attachment angle when the loupe is attached to the carrier lens.

As illustrated in FIG. 5, the downward attachment angle r can be calculated by the forward tilting angle α of the carrier lens 5 and angle β. The following describes how to calculate the forward tilting angle α.

When the marker 8 is viewed from the front in a state where the wearer faces downward and looks at the working operation point P, the lower side of the marker 8 is closer to the working operation point P than the upper side, so that the marker 8 looks like a trapezoidal shape in which the upper side thereof is shorter than the lower side as denoted by the continuous line of FIG. 10. At this time, the central control section 23 detects (X1, Y1), (X2, Y2), (X3, Y3), and (X4, Y4) as the coordinate positions of respective four corners A, B, C, and D of the recognized trapezoidal shaped marker 8. Here, the vertical and horizontal dimensions of the marker 8 having a square shape are previously input, so that the central control section obtains through arithmetic operation (X1', Y1'), (X2', Y2'), (X3', Y3'), and (X4', Y4') as the coordinate positions of four corners A, B, C, and D of the originally square-shaped marker 8 at a virtual position denoted by the broken line.

Thus, when the marker 8 is recognized as the trapezoidal shape, the height dimension a of the marker 8 can be represented by (Y1+Y3), the length b1 of the upper base thereof by (X1+X2), and the length b2 of the lower base thereof by (X3+X4). On the other hand, when the marker 8 is recognized as the square shape, the length a' of the vertical side of the marker 8 can be represented by (Y1'+Y3'), and the length b' of the horizontal side thereof by (X1'+X2').

The forward tilting angle α can be calculated according to the following expression using the values b1, b2, a', and b', where L in the expression denotes the distance from the working operation point P to a center point C of the marker 8 and is actually measured by a measuring means:

$$\alpha = \sin^{-1}\{(1/b1 - 1/b2) \times b'/a' \times L\}$$

Figure 11:
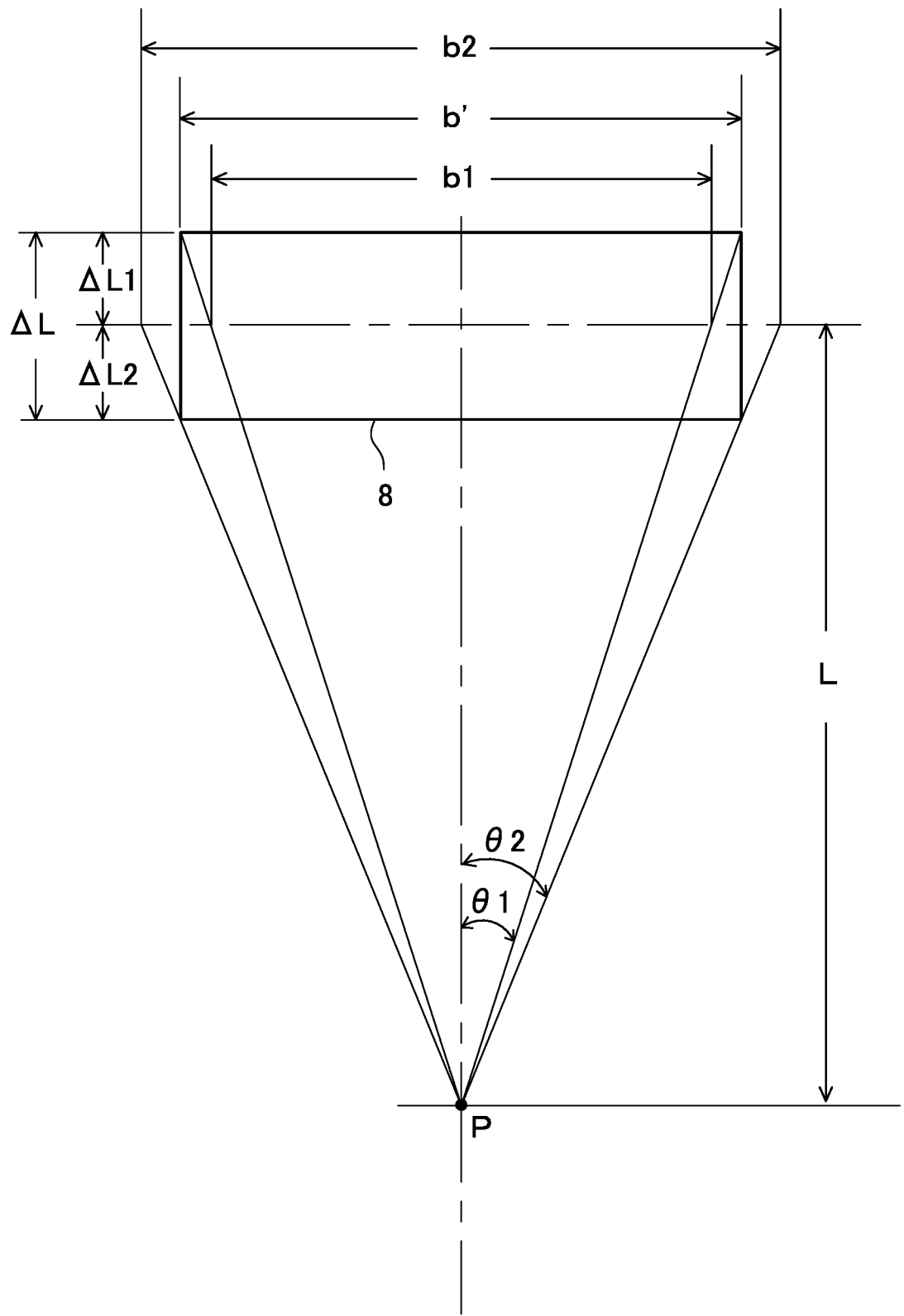
FIG. 11 is a plan view of the image of FIG. 10.

The following describes the above expression for calculating the forward tilting angle α. FIG. 11 is a plan view of the marker 8 as viewed from the working operation point P.

Figure 12:
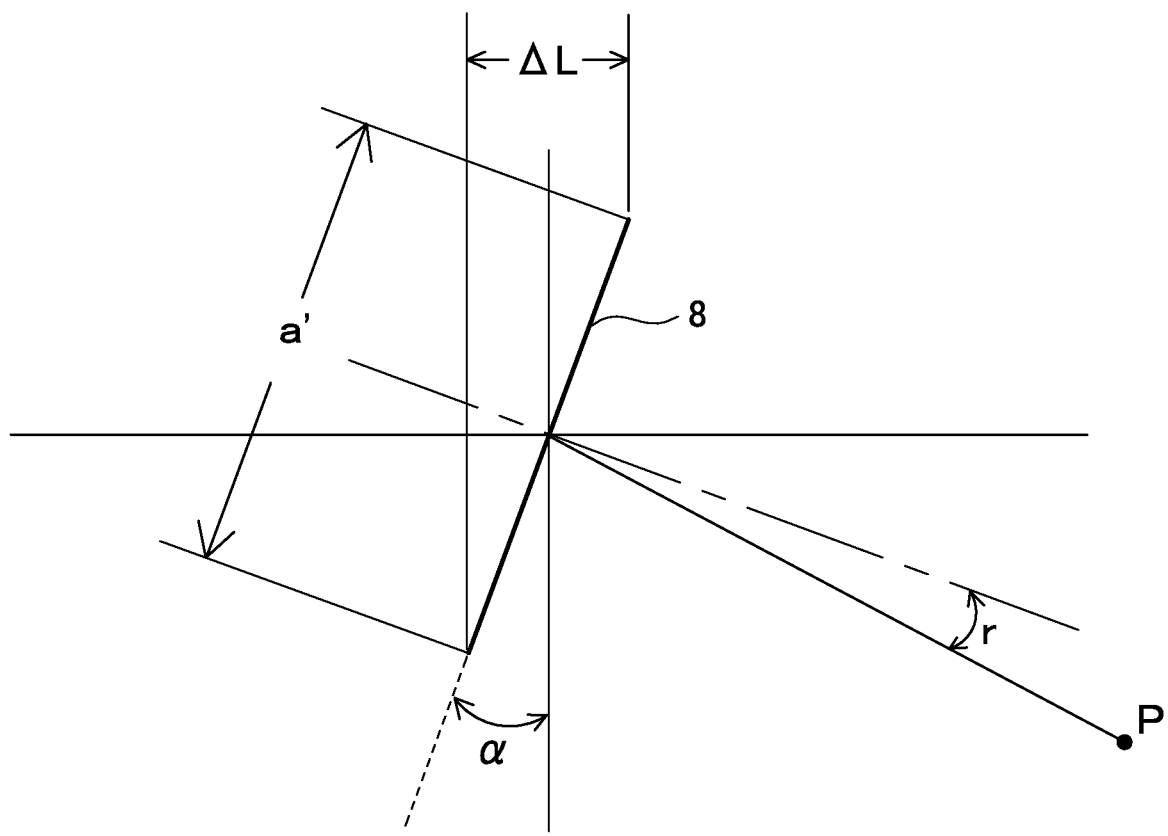
FIG. 12 is a side view of the image of FIG. 10.

(1) When the marker 8 is tilted as illustrated in FIG. 12, the vertical length thereof is represented by a'. At this time, when the length of the horizontal side of a right triangle having the vertical length a' as the oblique side is assumed to be ΔL, the forward tilting angle α is represented by the following expression:

$$\alpha = \sin^{-1}(\Delta L/a')$$

(2) The a' is known by actual measurement, so that the ΔL can be calculated. Then, when the ΔL is divided into ΔL1 and ΔL2 at the center point C of the marker 8, the following relationship is satisfied (FIG. 11):

$$\tan \theta 1 = (b1/2)/L = (b'/2)/(L+\Delta L1)$$

$$\therefore \Delta L1 = (b'/b1 - 1) \times L$$

$$\tan \theta 2 = (b2/2)/L = (b'/2)/(L-\Delta L2)$$

$$\therefore \Delta L2 = (1 - b'/b2) \times L$$

(3) Thus, the ΔL can be calculated as follows:

$$\Delta L = \Delta L1 + \Delta L2 = \{(b'/b1 - 1) + (1 - b'/b2)\} \times L = \{(1/b1 - 1/b2) \times b' \times L\}$$

(4) By calculating the ΔL, the above expression for calculating the forward tilting angle α is satisfied as follows:

$$\alpha = \sin^{-1}(\Delta L/a) = \sin^{-1}\{(1/b1 - 1/b2) \times b'/a' \times L\}$$

The distance L can be measured not only using a measuring means, but also by laser irradiation using a laser measurement device onto the center point C of the marker 8 from the working operation point P. Further, in addition to the above actual measurement, the distance L can be calculated according to the following expression using a focal length f at photographing, the actual measurement value of the length b' of the horizontal side, and an image size of the camera 11:

$$L = \{f \times (\text{actual size of marker 8})\}/(\text{image size of marker 8})$$

After the forward tilting angle α is thus calculated, the angle β is calculated by measuring the distance M from the working operation point P to the carrier lens 5 and the horizontal direction distance N orthogonal to the vertical line passing through the carrier lens 5, so that a downward attachment angle r can be derived.

[Determination of Inward Attachment Angles of Loupe]

Figure 14:
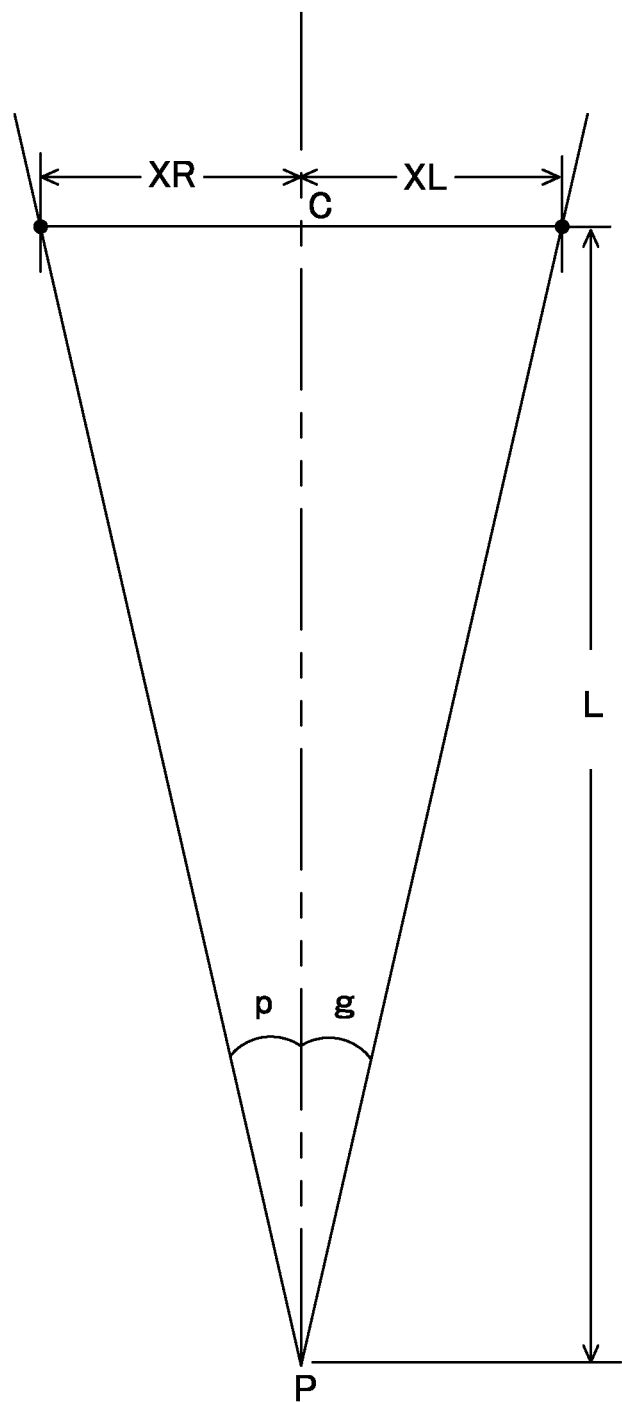
FIG. 14 is an explanatory view explaining how to detect inward attachment angles from left and right pupil positions.

As illustrated in FIG. 14, the inward attachment angles p and q when the left and right loupes 2 are attached to the carrier lens 5 are determined on the basis of the distances from the right and left pupil positions of the wearer to the center point C of the marker 8 in the X-direction and the distance L from the center point C to the working operation point P.

The distances from the left and right pupil positions of the wearer to the center point C in the X-direction are not changed even when the face of the wearer is tilted, so that the computer 20 can measure XR (for right pupil) and XL (for left pupil) from the coordinate positions of the respective right and left pupils. The distance L can be calculated by various methods as described above. Thus, the left and right inward attachment angles p and q can be calculated by the following respective expressions:

$$p = \tan^{-1}(L/XR)$$

$$q = \tan^{-1}(L/XL)$$

[Detection of Punching Position]

Figure 13A:
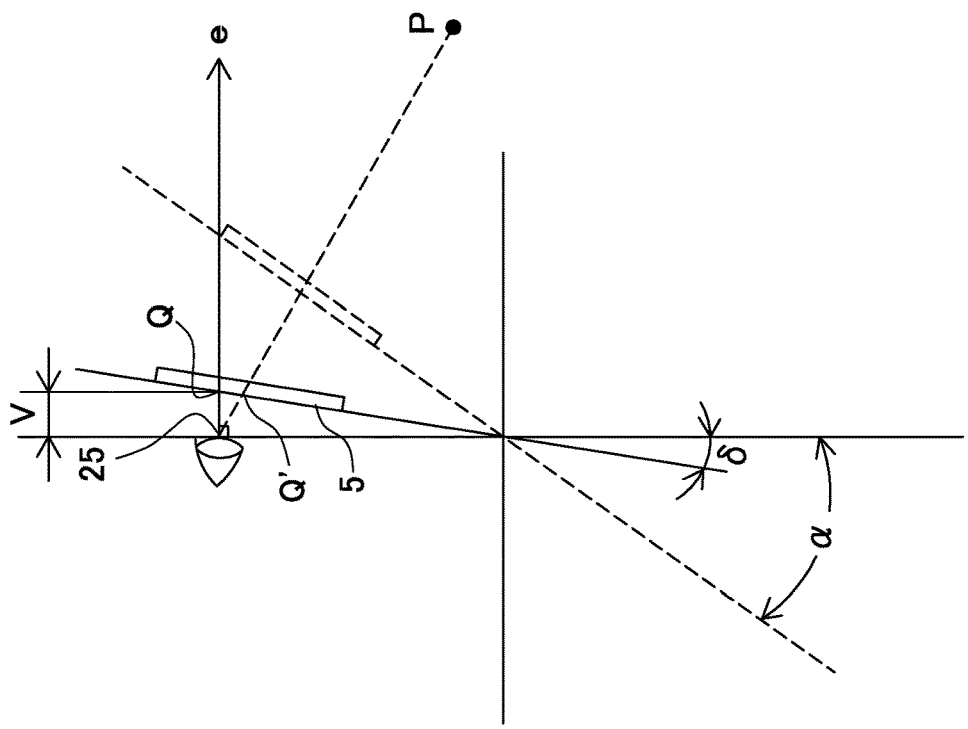
FIGS. 13A and 13B are schematic side views explaining the positional relationship among a pupil, the carrier lens, and the working operation point.
Figure 13B:
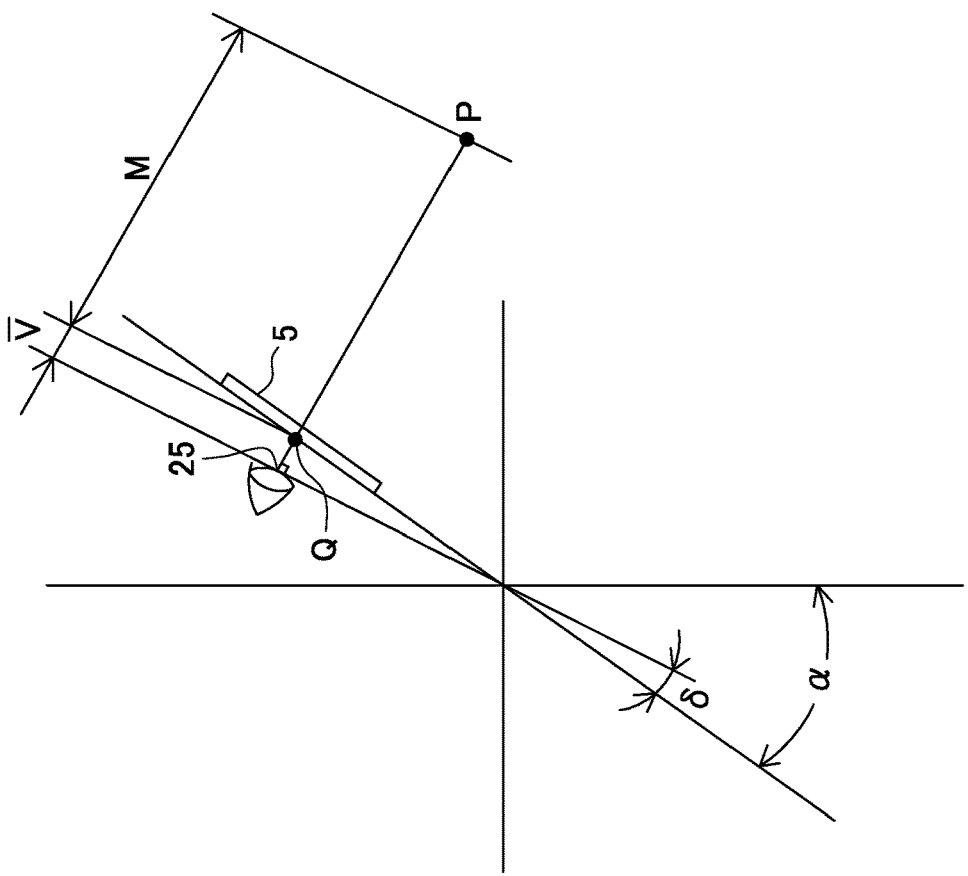
Figure 15:
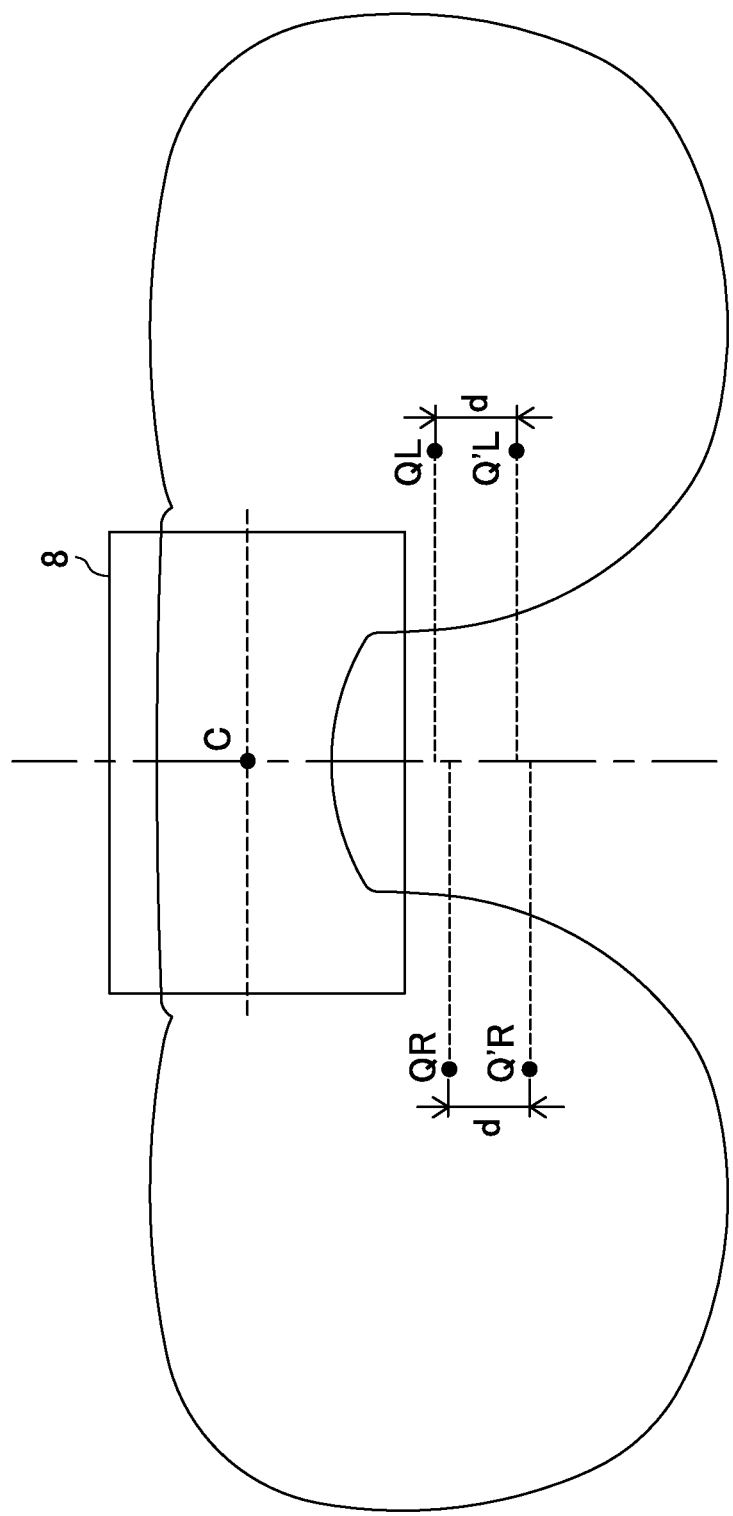
FIG. 15 is a front view for explaining the coordinate positions of the pupils on the surface of the carrier lens.

The following describes how to detect the punching position for attachment of the loupe 2 to the carrier lens 5 using FIGS. 13A and 13B and FIG. 15.

FIG. 13A illustrates a state where a user wearing the frame 1 tilts his or her body downward and looks at the working operation point P (that is, a cornea 25 of the pupil is directed to the working operation point P), and the coordinate position of a point Q on the surface of the carrier lens 5 connecting the cornea 25 and the working operation point P is QR (XR, YR) for the right pupil and QL (XL, YL) for the left pupil as illustrated in FIG. 15. The α and M are the forward tilting angle α and the distance from the working operation point P to the surface of the carrier lens 5, respectively, as described using FIG. 5. The frame 1 is designed such that the surface of the carrier lens 5 is tilted relative to the vertical line when a user wears the frame 1. The tilt angle of the carrier lens 5 is represented by δ. Further, the distance between the cornea vertex and the carrier lens 5 is represented by V. For the distance M, it is preferable to individually measure the distances from the working operation point P to the left and right carrier lenses 5 in terms of accuracy. The distance M can be actually measured using a measuring means or a laser measurement device or obtained through calculation based on a photographed image, as in the measurement of the distance L.

Then, when the frame wearer changes the forward tilting posture to direct the line of sight e in the horizontal direction as illustrated in FIG. 13B, the pupil is moved, and the cornea 25 is rotated upward by an angle of (α−δ). Accordingly, as illustrated in FIG. 15, each of the left and right pupil positions on the surface of the carrier lens 5 is moved by a distance d on the Y-coordinate axis. The distance d can be represented by $(V+M) \tan(\alpha-\delta)$.

Thus, the coordinate positions of the left and right pupils when the line of sight e is directed in the horizontal direction are as follows:

Q'R (XR, YR+(V+M) tan (α−δ))

Q'L (XL, YL+(V+M) tan (α−δ)), and these coordinate positions correspond to right and left punching positions Q'R and Q'L at each of which a hole is punched for attachment of the loupe 2 onto the carrier lens 5.

Figure 16:
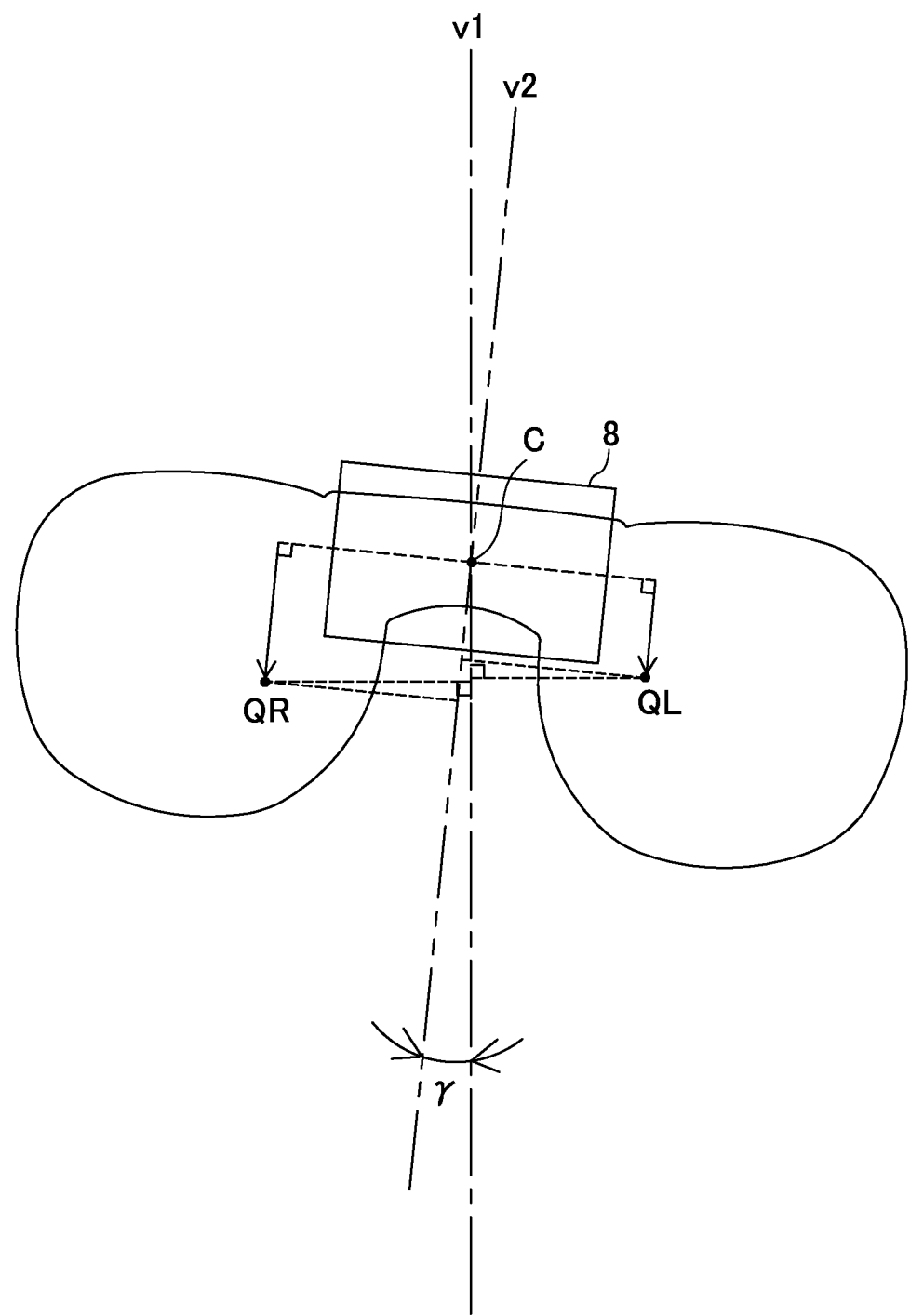
FIG. 16 is a schematic view explaining a state where a center line v1 of the face and the center line v2 of the frame are misaligned by tilting.
Figure 17:
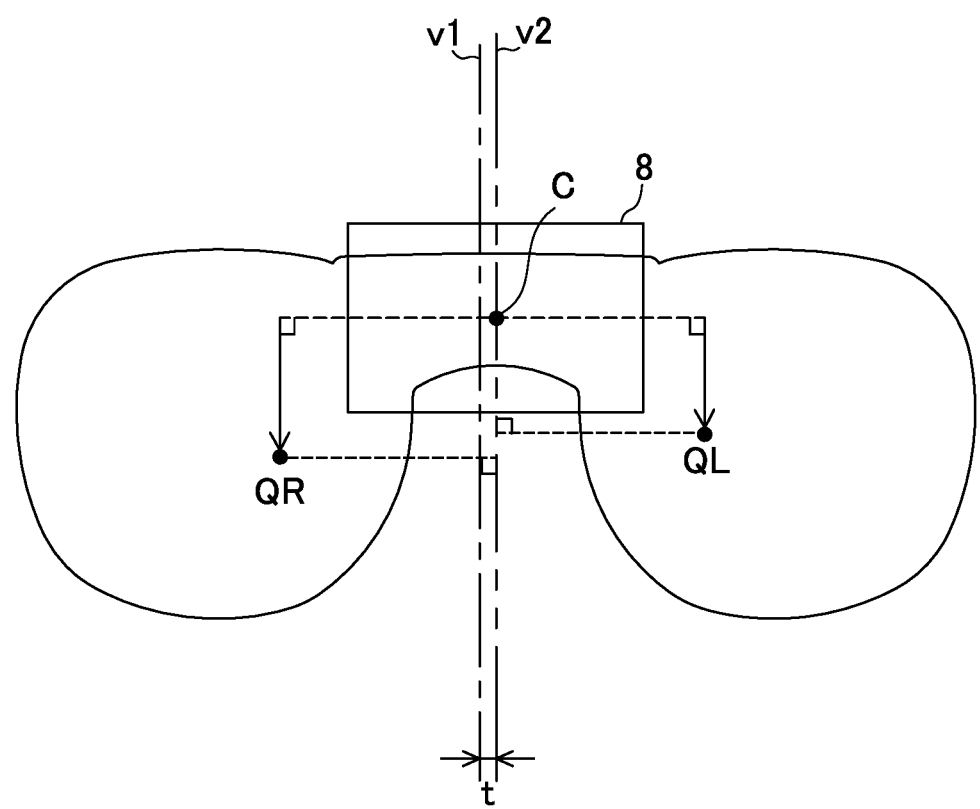
FIG. 17 is a schematic view explaining a state where the center line v1 of the face and center line v2 of the frame are misaligned in parallel with an interval therebetween.

When a user wearing a glasses frame is photographed, a center line v1 passing through the center of the wearer's face and a center line v2 passing through the center of the frame may not coincide with each other because of the physical feature of the wearer or adjustment error of the frame. In FIG. 16, the center line v2 is rotated in the clockwise direction about the center point C, that is, the center line v2 is tilted relative to the center line v1 by an angle γ. In FIG. 17, the center lines v1 and v2 are vertical lines, but extend in parallel at an interval t.

Thus, when the misalignment illustrated in FIG. 16 occurs, the central control section 23 performs the following correction when identifying the coordinate positions QR (XR, YR) and QL (YR, YL) of the right and left pupils:

QR (XR, YR+XR tan γ)

QL (XL, YL+XL tan γ)

The angle γ can be derived from a difference occurring between values of Y1 and Y2 at the coordinate positions of A and B (or C and D) of the corners of the marker 8.

When the misalignment illustrated in FIG. 17 occurs, the central control section 23 performs the following correction when identifying the coordinate positions QR (XR, YR) and QL (YR, YL) of the right and left pupils:

QR (XR+t, YR)

QL (XL−t, YL)

The interval t can be derived from a difference between the X-coordinate value at the intermediate position between the left and right pupils and the X-coordinate value of the center point C of the marker 8.

Thus, even when the misalignment occurs between the center line v1 of the face and the center line v2 of the frame, the central control section 23 can calculate the coordinate positions QR and QL of the right and left pupils with accuracy. In this case, even when the misalignments of FIG. 16 and FIG. 17 occur in combination, it is possible to cope with this by using the above corrections. That is, when the center lines v1 and v2 are misaligned in parallel with the interval t' therebetween even after the Y-coordinate values YR and YL of the right and left pupils are corrected on the basis of the angle γ, the X-coordinate values XR and XL of the right and left pupils are corrected on the basis of the interval t'.

[Production of Binocular Loupe]

Based on the thus determined punching position coordinates, the downward attachment angle r, and inward attachment angles p and q, the position at which the loupe 2 is inserted into the carrier lens 5 is programmed to an NC working machine, and the insertion position is subjected to cutting processing to hollow out the surface of the carrier lens 5 for formation of an opening. After formation of the opening, the loupe 2 is inserted into the carrier lens 5 through the opening. Then, a laser positioner is used to adjust the downward attachment angle r and inward attachment angles p and q, and the loupe 2 is fixed to the carrier lens 5 through the attachment part 3. The attachment part 3 is constituted of an adaptor for fixing the loupe 2 and a ring for fastening the adaptor with the carrier lens 5 interposed therebetween. The adaptor is designed to retain the loupe 2 at the downward attachment angle r, and inward attachment angles p and q relative to the surface of the carrier lens 5. Alternatively, the loupe 2 may be fitted into the opening of the carrier lens 5 while maintaining the downward attachment angle r, and inward attachment angles p and q and bonded by an adhesive material.

The present invention relates to a binocular loupe used for medical surgery or precision machining and, more particularly to a production method for a binocular loupe designed to accommodate itself to the left and right pupil positions and working postures corresponding to the features of individual workers and has industrial applicability.

What is claimed is:

1. A binocular loupe production method that produces a binocular loupe by attaching a loupe to a carrier lens fitted to a frame while a user wears the binocular loupe, the method comprising:
    (a) a step of attaching a square marker to the frame;
    (b) a step of photographing, from a working operation point (P) located below, a face of a frame wearer who looks at the working operation point (P) while assuming a working posture taken when he or she is using the binocular loupe;
    (c) a step of detecting a face photographed image from the photographed image, and a trapezoidal shape of the marker by converting the face photographed image into polylines and extracting, from objects each having four corners, an object in which an angle of each of the four corners is nearly 90°;
    (d) a step of calculating a forward tilting angle (α) of the carrier lens according to a degree of change from a square shape to the trapezoidal shape of the marker detected in the step (c) and determining, based on the forward tilting angle (α), a downward attachment angle (r) based on which the loupe is attached to the carrier lens.

2. The binocular loupe production method according to claim 1, wherein in the step (c), X- and Y-axes coordinate positions of the four corners of the marker in an oblique image are determined.

3. The binocular loupe production method according to claim 2, wherein in the step (c), a coordinate position of a center of the marker is detected from the coordinate positions of the four corners thereof.

4. The binocular loupe production method according to claim 2, wherein in the step (c), the number of pixels per unit dimension in a detection image is calculated from a known actual dimension of the marker, and values of X and Y of the coordinate positions are represented by the number of pixels, respectively.

5. The binocular loupe production method according to claim 2, wherein in the step (d), the forward tilting angle (α) is determined on a basis of dimensions of upper and lower bases of the trapezoidal shape derived from the coordinate positions, ratio of actual vertical and horizontal dimensions of the marker, and a distance from the working operation point (P) to a center point (C) of the marker.

6. The binocular loupe production method according to claim 1, wherein in the step (d), the downward attachment angle (r) is determined according to a complementary angle of an angle formed by a line extending from the working operation point (P) to the carrier lens which is previously measured as a distance (M) and a horizontal line orthogonal to a vertical line passing through the carrier lens which is previously measured as a distance (N) and the forward tilting angle (α).

7. The binocular loupe production method according to claim 1, further comprising (e) a step of identifying, from the image, X- and Y-axes coordinate positions of respective right pupil (XR, YR) and left pupil (XL, YL) of the frame wearer who looks at the working operation point (P) located below.

8. The binocular loupe production method according to claim 7, wherein in the step (e), the positions of the pupils are detected by identifying, from the image, a position where brightness changes discontinuously.

9. The binocular loupe production method according to claim 8, wherein in the step (e), face detection is performed by extracting image features unique to the face from the photographed image, followed by detection of pupil positions from a detected face.

10. The binocular loupe production method according to claim 9, wherein in the step (e), image features unique to an eye is extracted from the detected face.

11. The binocular loupe production method according to claim 10, wherein in the step (e), a contour of an iris is detected by binarizing a detection image of the eye.

12. The binocular loupe production method according to claim 11, wherein in the step (e), a morphology processing is performed to detect a rectangle having a maximum brightness to detect the pupil positions.

13. The binocular loupe production method according to claim 7, further comprising (f) a step of determining an attachment position of the loupe to the carrier lens on a basis of the coordinate positions of the respective right pupil (XR, YR) and left pupil (XL, YL).

14. The binocular loupe production method according to claim 13, wherein in the step (f), a Y-coordinate value of the loupe attached to the carrier lens is below Y-coordinate values of the respective left and right pupils.

15. The binocular loupe production method according to claim 14, wherein in the step (f), the Y-coordinate value of the loupe attached to the carrier lens is determined on a basis of an angle at which the frame wearer turns his or her cornea upward to direct a line of sight in a horizontal direction.

16. The binocular loupe production method according to claim 15, wherein in the step (f), the angle at which the cornea is turned upward is determined on a basis of the forward tilting angle (α) and a tilt angle (θ) of the carrier lens relative to a vertical line.

17. The binocular loupe production method according to claim 16, wherein in the step (f), the Y-coordinate value of the loupe attached to the carrier lens is determined further on a basis of a distance (V) between the cornea and the carrier lens and a distance (M) from the working operation point (P) to a surface of the carrier lens.

18. The binocular loupe production method according to claim 17, wherein the distance (M) from the working operation point (P) to the surface of the carrier lens is actually measured by a distance measuring sensor using ultrasonic waves or infrared rays.

19. The binocular loupe production method according to claim 13, wherein in the step (f), the coordinate positions of the respective right pupil (XR, YR) and left pupil (XL, YL) are corrected on a basis of a misalignment between a center line (v1) passing through a center of the wearer's face in a vertical direction and a center line (v2) passing though a center of the marker in the vertical direction.

20. The binocular loupe production method according to claim 19, wherein in the step (f), when the center line (v1) and the center line (v2) are misaligned so as to cross each other, a Y-coordinate value (YR, YL) of the pupil is corrected on a basis of an angle (γ) at which the center lines (v1) and (v2) cross each other.

21. The binocular loupe production method according to claim 19, wherein in the step (f), when the center line (v1) and the center line (v2) are misaligned in parallel with an interval (t) therebetween, a X-coordinate value (XR, XL) of the pupil is corrected on a basis of the interval (t).

22. The binocular loupe production method according to claim 21, wherein the interval (t) is calculated from difference between the X-coordinate value of an intermediate position of the left and right pupils and the X-coordinate value of a center point (C) of the marker.

23. The binocular loupe production method according to claim 21, wherein in the step (f), when the center lines (v1) and (v2) are misaligned in parallel with an interval (t') therebetween even after a Y-coordinate value (YR, YL) of the pupil is corrected on a basis of an angle (γ), the X-coordinate value (XR, XL) of the pupil is corrected on a basis of the interval (t').

24. The binocular loupe production method according to claim 19, wherein the attachment position of the loupe to the carrier lens is determined according to a corrected coordinated position (XR, YR) of the right pupil and a corrected coordinated position (XL, YL) of the left pupil obtained in the step (f).

25. The binocular loupe production method according to claim 24, wherein in the step (f), a Y-coordinate value of the loupe attached to the carrier lens is below Y-coordinate values of the respective left and right pupils.

26. The binocular loupe production method according to claim 25, wherein in the step (f), the Y-coordinate value of the loupe attached to the carrier lens is determined on a basis of an angle at which the frame wearer turns his or her cornea upward to direct a line of sight in a horizontal direction.

27. The binocular loupe production method according to claim 26, wherein in the step (f), the angle at which the cornea is turned upward is determined on a basis of the forward tilting angle (α) and a tilt angle (θ) of the carrier lens relative to a vertical line.

28. The binocular loupe production method according to claim 27, wherein in the step (f), the Y-coordinate value of the loupe attached to the carrier lens is determined further on a basis of a distance (V) between the cornea and the carrier lens and a distance (M) from the working operation point (P) to the carrier lens.

29. The binocular loupe production method according to claim 28, wherein the distance (M) from the working operation point (P) to carrier lens is actually measured by a distance measuring sensor using ultrasonic waves or infrared rays.

30. The binocular loupe production method according to claim 13, further comprising (g) a step of determining inward attachment angles (p and q) of the loupes to be attached to left and right carrier lenses on a basis of distances from the right and left pupil positions to a center point (C) of the marker in a X-coordinate direction and a distance (L) from the center point (C) to the working operation point (P).

31. The binocular loupe production method according to claim 30, further comprising (h) a step of forming openings on surfaces of the respective left and right carrier lenses on a basis of the attachment position of the loupe to the carrier lens, the downward attachment angle (r), and the inward attachment angles (p and q) and inserting and fixing the left and right loupes into the openings.

32. The binocular loupe production method according to claim 31, wherein formation of the openings for attachment of the left and right loupes in the step (h) is made by cutting the surfaces of the carrier lenses using an NC working machine.

33. The binocular loupe production method according to claim 30, wherein when the left and right loupes are attached to the openings formed in the left and right carrier lenses in the step (h), a laser positioner is used to adjust the downward attachment angle (r) and the inward attachment angles (p and q), and the left and right loupes are inserted into and fixed to the openings of the left and right carrier lenses.

\* \* \* \* \*